US00RE40365E

(19) United States
(12) Reissued Patent
Kirchgeorg et al.

(10) Patent Number: US RE40,365 E
(45) Date of Reissued Patent: Jun. 10, 2008

(54) PORTABLE EMERGENCY OXYGEN AND AUTOMATIC EXTERNAL DEFIBRILLATOR (AED) THERAPY SYSTEM

(75) Inventors: John Kirchgeorg, Milwaukee, WI (US); Richard C. Turner, Arlington, VA (US)

(73) Assignee: Life Corporation, Milwaukee, WI (US)

(21) Appl. No.: 10/727,328

(22) Filed: Dec. 3, 2003

Related U.S. Patent Documents

Reissue of:
(64) Patent No.: 6,327,497
Issued: Dec. 4, 2001
Appl. No.: 09/151,300
Filed: Sep. 11, 1998

U.S. Applications:
(63) Continuation of application No. 10/457,958, filed on Jun. 10, 2003, now Pat. No. Re. 38,533.

(51) Int. Cl.
*A61M 16/00* (2006.01)
*A61B 19/00* (2006.01)
*A61N 1/00* (2006.01)
*A61J 1/00* (2006.01)

(52) U.S. Cl. ..... 128/205.22; 607/5; 607/3; 128/204.22; 128/204.23; 128/205.23; 128/897; 206/572

(58) Field of Classification Search ..... 128/202.22, 128/204.22–204.23, 205.22–205.23, 201.18, 128/204.21, 204.26, 205.11; 600/309, 323, 600/532
See application file for complete search history.

(56) References Cited

U.S. PATENT DOCUMENTS 3,613,677 A * 10/1971 Blasko ..... 128/204.21
4,109,828 A * 8/1978 Stewart ..... 222/3
4,197,842 A * 4/1980 Anderson ..... 128/203.12
4,198,963 A * 4/1980 Barkalow et al. ..... 601/106
4,241,833 A * 12/1980 Luebcke ..... 206/570
4,257,415 A * 3/1981 Rubin ..... 128/200.21
4,359,048 A * 11/1982 Almasi et al. ..... 128/205.12
4,438,764 A * 3/1984 Eppolito ..... 128/205.22
4,685,456 A * 8/1987 Smart ..... 128/205.22
4,739,913 A * 4/1988 Moore ..... 224/643
4,788,973 A * 12/1988 Kirchgeorg et al. ... 128/204.18
4,889,116 A * 12/1989 Taube ..... 128/204.23
4,932,402 A * 6/1990 Snook et al. ..... 128/204.23
4,944,292 A * 7/1990 Gaeke et al. ..... 128/204.18
5,207,303 A * 5/1993 Oswalt et al. ..... 190/108

(Continued)

OTHER PUBLICATIONS

"First Save: The simple, safe and affordable life saving solution", Survival Ink Corporation, 1997.*
"It's a fire extinguisher your people can use to put out a cardiac arrest", Phisio–Control Corporation, 1998.*
"When survival is measured in minutes", Heartstream, Inc. 1996.*
"CPR Prompt—AED/CPR Total Trainer", CPR Prompt, Inc., Jan. 1996.*
"paraPAC is for CPR", pneuPAC, Inc., 1998.*

*Primary Examiner*—Carl Layno
(74) *Attorney, Agent, or Firm*—Jones, Tullar & Cooper, P.C.

(57) ABSTRACT

This invention provides a medical diagnosis and therapy system particularly adapted for the combined uses of emergency cardiac defibrillation and pulmonary oxygen administration, including automated patient cardiopulmonary assessment and voice prompted therapy and resuscitation: electrocardio diagnosis/monitoring/defibrillation and electropulmonary blood oximetry/oxygen administration. The system has a case having access opening(s) and clear cover(s) to view the apparatus and contents, to dispel all doubt as to know how to open the case and to make it easy for a user to quickly find and use the various components.

21 Claims, 4 Drawing Sheets

U.S. PATENT DOCUMENTS 5,243,975 A * 9/1993 Alferness et al. ..... 607/7
5,308,320 A * 5/1994 Safar et al. ..... 604/6.14
5,494,051 A * 2/1996 Schneider, Sr. ..... 5/625
5,529,063 A * 6/1996 Hill ..... 600/573
5,549,659 A * 8/1996 Johansen et al. ..... 607/60
5,605,150 A * 2/1997 Radons et al. ..... 600/300
5,626,131 A * 5/1997 Chua et al. ..... 128/204.23
5,626,151 A * 5/1997 Linden ..... 128/897
5,653,685 A * 8/1997 Klatz et al. ..... 604/26
5,662,690 A * 9/1997 Cole et al. ..... 607/5
5,682,877 A * 11/1997 Mondry ..... 128/204.23
5,700,281 A * 12/1997 Brewer et al. ..... 607/5
5,706,801 A * 1/1998 Remes et al. ..... 128/202.26
5,716,380 A * 2/1998 Yerkovich et al. ..... 607/5
5,749,902 A * 5/1998 Olson et al. ..... 607/5
5,749,913 A * 5/1998 Cole ..... 607/59
5,782,878 A * 7/1998 Morgan et al. ..... 607/5
5,785,043 A * 7/1998 Cyrus et al. ..... 600/525
5,792,190 A * 8/1998 Olson et al. ..... 607/5
5,797,969 A * 8/1998 Olson et al. ..... 607/5
5,895,354 A * 4/1999 Simmons ..... 600/301
5,918,331 A * 7/1999 Hall et al. ..... 5/626
5,975,081 A * 11/1999 Hood et al. ..... 128/845
6,046,046 A * 4/2000 Hassanein ..... 435/284.1
6,142,962 A * 11/2000 Mollenauer et al. ..... 601/41
6,186,977 B1 * 2/2001 Andrews et al. ..... 604/67
6,199,550 B1 * 3/2001 Wiesmann et al. .... 128/204.23
6,325,978 B1 * 12/2001 Labuda et al. ..... 422/84
6,532,958 B1 * 3/2003 Buan et al. ..... 128/204.23
6,606,993 B1 * 8/2003 Wiesmann et al. .... 128/204.23
2002/0195105 A1 * 12/2002 Blue et al. ..... 128/204.21
2004/0074495 A1 * 4/2004 Wickhman et al. .... 128/204.18

* cited by examiner

PORTABLE EMERGENCY OXYGEN AND AUTOMATIC EXTERNAL DEFIBRILLATOR (AED) THERAPY SYSTEM

Matter enclosed in heavy brackets [ ] appears in the original patent but forms no part of this reissue specification; matter printed in italics indicates the additions made by reissue.

*CROSS REFERENCE TO RELATED APPLICATIONS*

*This reissue application is a continuation of Reissue Application Ser. No. 10/457,958, which is an application for reissue of U.S. Pat. No. 6,327,497, which reissue application has now issued as Reissue Pat. No. 38,533. In addition, two other continuation of Reissue Application Ser. No. 10/457,958 were also filed with the subject application on Dec. 3, 2003. U.S. Reissue Application Ser. No. 10/727,325 has recently been allowed to lapse, while U.S. Reissue Application Ser. No. 10/727,327 remains pending.*

BACKGROUND OF THE INVENTION

1. Field of the Invention

The present invention relates to an emergency medical diagnosis and therapy system integrating several emergency medical equipment components into a single multifunctional unit within a convenient unitary casing, so that medical personnel can easily handle, access and implement a variety of important emergency tools and therapies.

2. Description of the Related Art

Conventional emergency medial equipment has been improved over the years to advance the ability of emergency medical personnel to administer vital care to patients. Such advancements include voice prompting, automated and individualized patient assessments and self-maintenance of the equipment.

For example, a variety of small, portable on-site devices are available for administering electric pulse therapy in emergency situations of myocardial infarcation and to defibrillate and restart regular heart pump rhythms necessary for sustaining the life of the patient. Most of these Automatic External Defibrillator (AED) devices include electro-cardio diagnosis and monitoring of the patient, and many include voice prompting for the user. There are also known $O_2$ and $CO_2$ oximetry and capnography devices for measuring arterial oxygenation, perfusion, $O_2Hb$ dissociation, tissue $O_2$ affinity, $O_2$ content, $PO_2$, pulse oximetry saturation ($SPO_2$), or calculated oxygen saturation ($\%SO_2$), because oxygen supplementation is critical in many emergency cardiopulmonary trauma situations. For this latter purpose, there exist a wide variety of oxygen resuscitators, inhalators, or ventilators.

Often, first responder medical personnel have arrived on site to attend the victim with an AED defibrillator, but have been unable to resuscitate and keep alive the victim without supplemental oxygen on hand. In many instances the victim was successfully defibrillated, but poor cell perfusion and toxic gases due to hypoxia prevented successful recovery. In many other instances, the first responder arrived when the vital signs of the victim were declining but could do little until after the victim had begun defibrillation or expired. In the first instances, supplemental oxygen administration may have insured successful survival of the defibrillated victim. In the second instances, supplemental oxygen administration may have even precluded the need for the defibrillator. In both instances, emergency oxygen may have saved the victim by restoring the proper oxygenation and cell perfusion necessary for survival.

Heretofore, each piece of emergency equipment has typically been contained in its own housing or carrying case and used independently, as a stand-alone unit. Handling each piece of equipment separately, however, is inconvenient and cumbersome for medical personnel, who are often situated in awkward conditions and dangerous circumstances, such as at automobile accident sites. Moreover, the use of separate units ignores the interdependence of administration among the several emergency systems.

SUMMARY OF THE INVENTION

Accordingly, the present invention improves upon conventional arrangements by providing a medical care system comprising a plurality of interdependent emergency medical systems in one convenient unit.

An object of the invention is to provide a multifunctional emergency medical care system which places a plurality of interdependent emergency therapy devices in a single unit, and which is capable of guiding emergency medical personnel through emergency procedures which employ these devices simultaneously.

A further object of the invention is to provide an emergency medical therapy system having various devices which may be needed in a medical emergency, arranged in a housing unit in a manner allowing easy and convenient simultaneous access to each piece of equipment so that the user can utilize the equipment easily, quickly and efficiently.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENTS

Reference will now be made in detail to the preferred embodiments of the present invention, examples of which are illustrated in the accompanying drawings.

Figure 1:
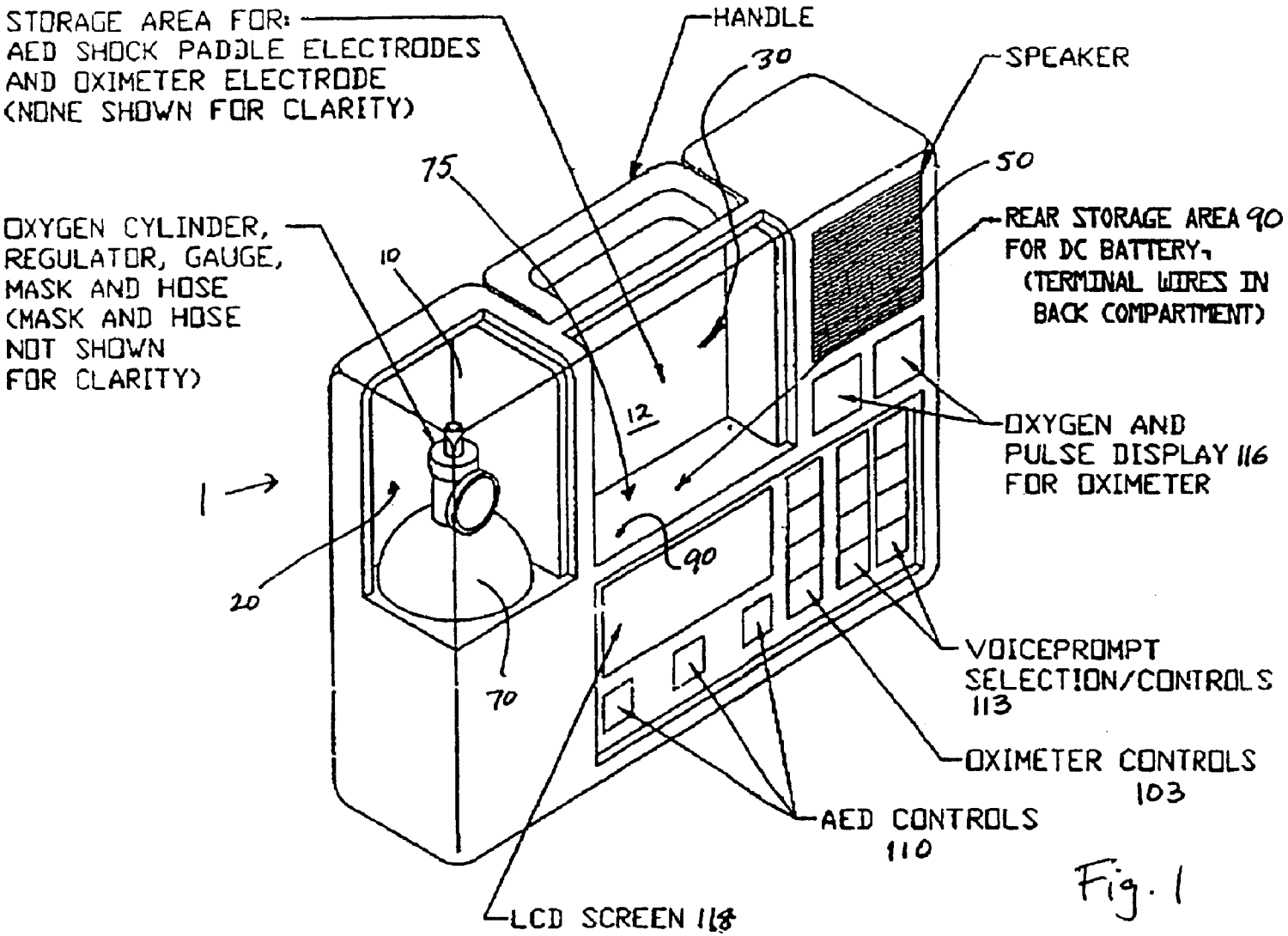
FIG. 1 is a perspective view illustrating a first embodiment of the system.

Referring to FIG. 1, the first embodiment illustrates a housing 1 having two access openings for accessing two compartments 20, 30. Two clear or opaque covers 10, 12 cover the openings, respectively.

Handle 40 provides a means for carrying the unit to a victim or patient. This allows the user to have a free hand for other equipment, handling a patient or other important tasks.

Moreover, with multiple pieces of equipment housed in the same unit, the user needs to only look at the face of the unit to view the various displays for the different systems.

Thus, consolidating multiple medical devices into one unit provides easier handling and convenience for the user.

Figure 2:
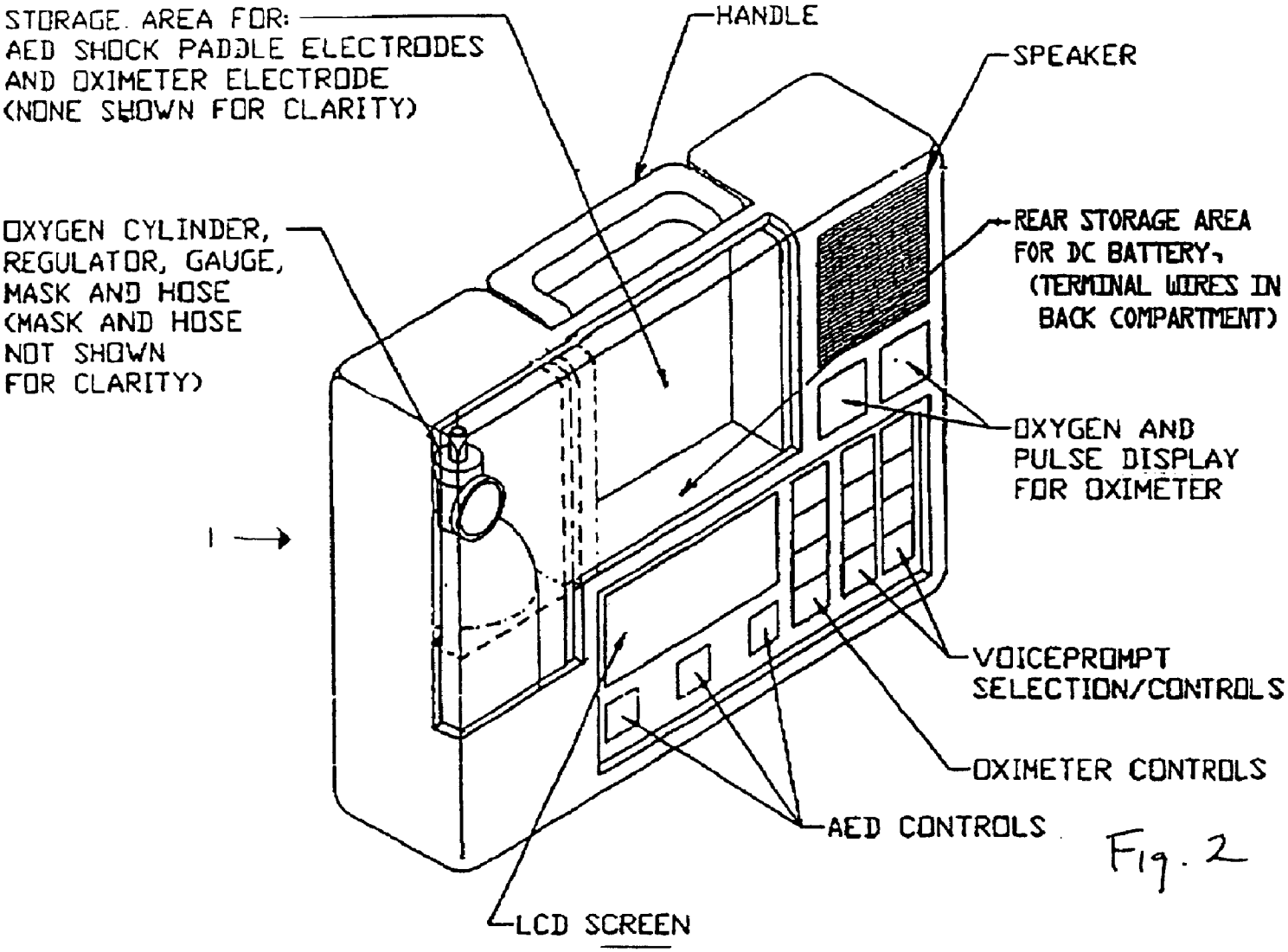
FIGS. 2 and 3 are perspective views illustrating variations of the embodiment of the system.

A convenient variation is illustrated in FIG. 2. Instead of having two covers, this embodiment has one cover 14 for covering the openings of compartments 20, 30. In this embodiment, only a single cover 14 is removed to access the various compartments of the housing 1.

This provides an advantage over the first embodiment since the user only needs to remove a single cover to access all the equipment. During an emergency, when time is of the essence, this provides an important advantage for the user of saving time. The rest of this variation is similar to the first embodiment and thus, the features are represented by the same reference numerals and a detailed description is omitted.

Figure 3:
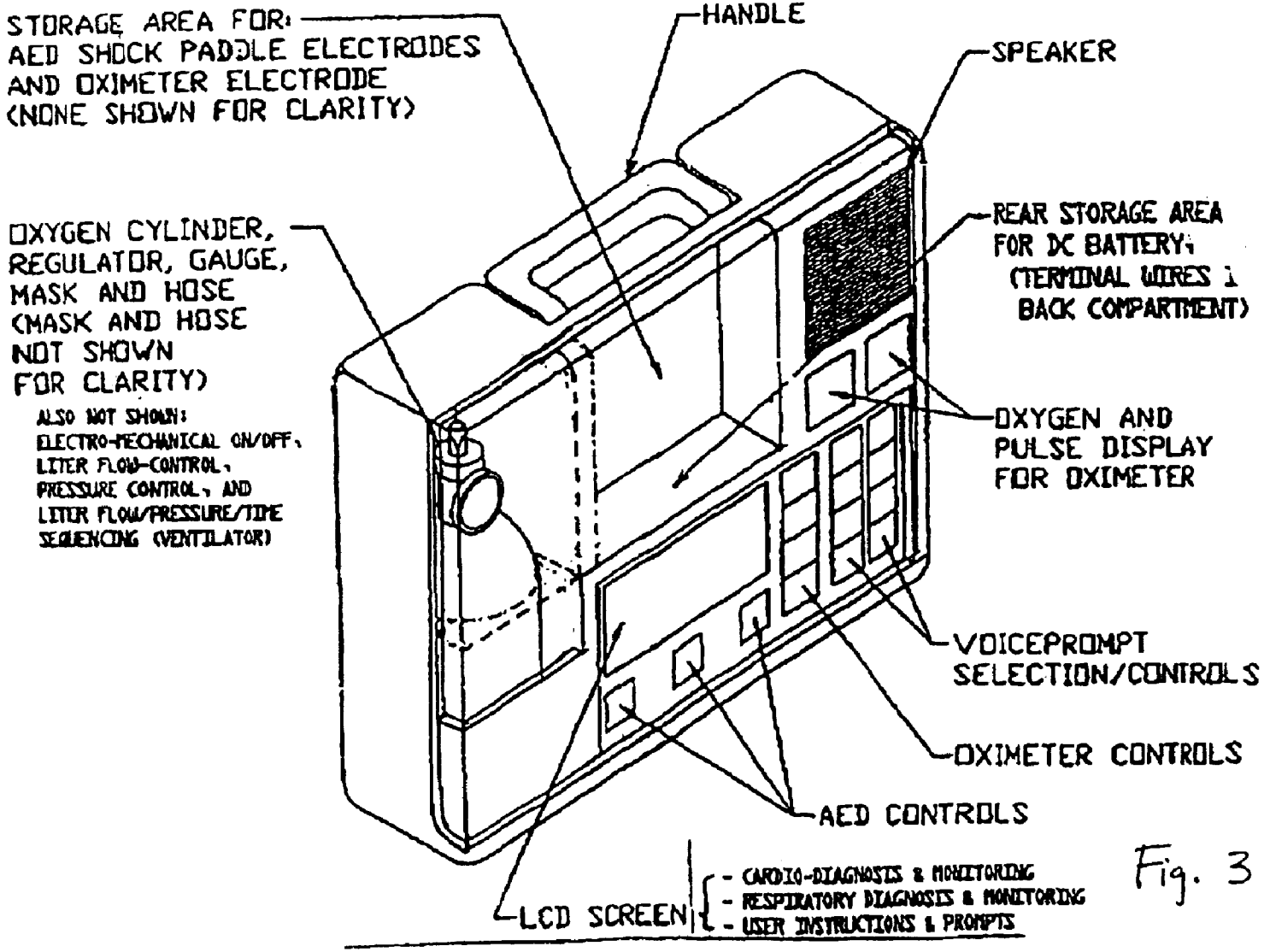

FIG. 3 illustrates another variant of the invention. A single cover 16 covers the entire front face of the housing 1. Thus, all the equipment pieces, including the displays and controls are covered with a preferably clear cover 16.

This variation provides an advantage over the first and second described in units in that the displays 80, speaker 50, and other various controls 60 are protected by the cover 16. Thus, during use the operator only needs to remove a single cover piece to access all components in the housing. After use, the single cover protects all the controls and displays, as well as the other equipment housed in the compartments from damage during storage or transport.

As noted above, each compartment 20, 30 holds one or more emergency medical devices. Several component variations are possible. For instance, the housing may combine a small-sized emergency oxygen unit (gas dispensing device) with an oximeter, a pulse display and electrode lead. As another alternative, either or both of the emergency oxygen unit and oximetry system may be combined with an Automatic External Defibrillator (AED), corresponding controls and paddle electrodes. In either case, the system may include a voice prompt system, selection controls and a speaker. Many other combinations are possible, as will be evident to those of skill in the art.

FIG. 1 shows housing 1 having a gas dispensing device 70 and an electrocardio defibrillation device 75, the former comprising an oxygen cylinder with a mechanical or electromechanically controlled regulator, gauge, mask and hose in one compartment 20.

The oxygen dispensing device may be functional in two modes: manual mode, in which an on/off switch or lever simply controls on/off supply of oxygen, generally delivered at a fixed or variable low flow rate, or automatic mode, where the flow rate is variable and may be controlled either according to program control or via feedback from the oximetry unit. Included within the variable flow rate mode may be a ventilation mode for non-breathing victims, wherein liter flow and pressure are subjected to time sequencing according to a cycle corresponding closely to requirements the victim needs to return to a normal breathing pattern. Compartment 30 stores defibrillator shock paddle electrodes 121 and oximeter electrode 107. Several other component variations are also possible.

The defibrillation device and associated controls are contained entirely within the housing 1, and may be of a form known in the art, as represented by U.S. Pat. Nos. 5,797,969, 5,792,190, 5,749,902, 5,700,281, 5,716,380, 5,605,150, 5,549,659, 5,529,063, 5,243,975, 5,785,043, 5,782,878, 5,749,913 and 5,662,690, each of which is incorporated by reference herein. Several of these known defibrillators include voice prompting; the invention deviates from the known voice prompting scheme in that it also includes timely prompts for oximetry measurement and the administration of oxygen. The protocols for the coordination of oximetry, oxygen administration and defibrillation are known generally in the medical arts, and therefore will not be explained in detail here.

Housing 1 holds power source 90 (battery), and the known controls 110, 103 and displays 116, 118 for the defibrillator and oximeter. A speaker 50 is also housed in the housing 1, to be used in conjunction with voice prompting tools and controls 113.

An example of the use of the invention will now be described, in order to better explain the functionality of the invention.

At an accident scene, for example, it is determined that a victim is currently in cardiac arrest. Upon enabling the unit of the invention, controls 113 may be activated to enable the voice prompt system, which will guide the user through the steps necessary to operate the oxygen delivery, oximetry and defibrillation systems. Such voice prompt systems are known in the portable defibrillation arts, however, according to the invention the prior art system may be modified to include prompts for effecting oxygen administration and oximetry measurements.

For example, in this example of a non-breathing victim in cardiac arrest, the voice prompt system may guide the user through the following protocols:

initiate and deploy defibrillation system and paddles administer electroshock treatment initiate oxygen delivery in ventilator mode deploy oximetry measuring electrode.

If the defibrillation is successful, as determined by a pulse reading, the voice prompt system may subsequently guide the user through switching of the ventilator mode to a regulated constant volume oxygen delivery mode which is more suitable for a breathing patient, and/or make other variations in oxygen delivery via program control or in response to oximetry readings. Naturally, many variations are possible as will be readily apparent to those of skill in the art.

In its most simple form, the integrated emergency medical systems of the invention may be substantially without interdependent control. For example, an emergency oxygen device can be combined with a defibrillation system, without any electromechanical connection therebetween. In such a case, if voice prompting is added, the system may prompt only for defibrillation, or both defibrillation and oxygen delivery, for example.

Figure 4:
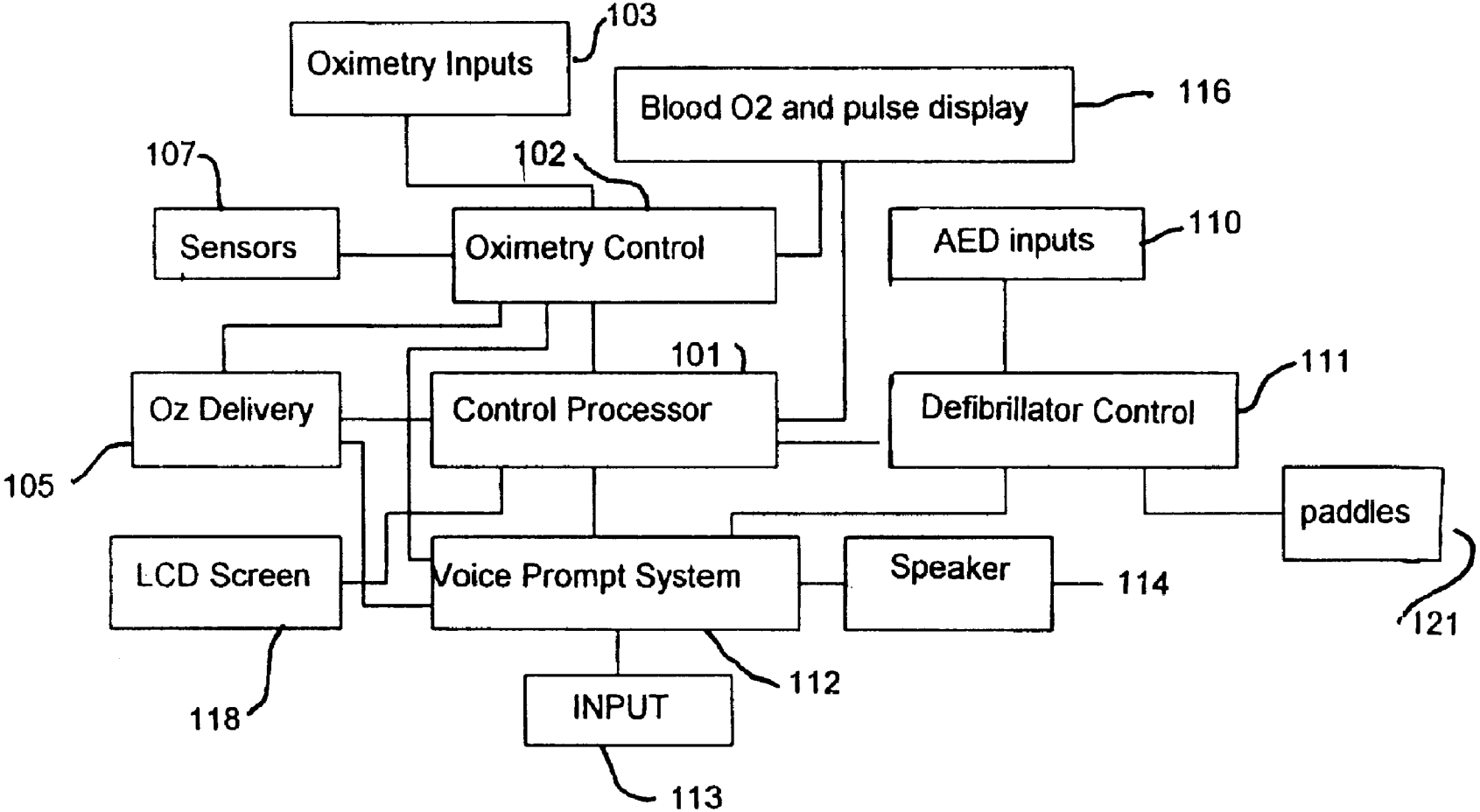
FIG. 4 is a system diagram of a fully integrated emergency medial system.

A more integrated and sophisticated system is illustrated in FIG. 4. In this system, a control processor controls operation of the various emergency medical units (oxygen delivery, defibrillation and oximetry), accepts feedback from each of these units, interfaces with and controls the voice prompt system, and drives the various displays 116, 118. When the operator selects AED or oximetry functions by operating inputs 103, 110, the processor controls defibrillator control 111 to generate an output waveform of a selected type in accordance with operator selection, and controls oximetry control section 102 in accordance with operator selection to perform various measurements and drives display 116 to display these measurements, e.g., pulse rate and blood $O_2$ related measurements, to the operator in real time. Similarly, processor 101 drives LCD screen 118 to display user instructions and prompts, respiratory monitoring and diagnosis, and cardio diagnosis and monitoring data.

Processor 101 also interfaces with voice prompt system 112 to cause the latter to deliver a selected sequence of voice prompts via speaker 114 according to predetermined protocols, operator input and the condition of the patient as measured by the system, including sensor 107, in a manner generally similar to that known in the art.

As noted previously, the oxygen delivery system 105 can be controlled either manually or by automatic control. In a manual mode, for example, the system 105 may deliver oxygen at a fixed liter flow and pressure, or at a plurality of flow rates. In automatic mode, the system 105 may, in response to a control signal from processor 101 (or user input), deliver a time sequenced flow rate and pressure to operate as a ventilator. In response to user input, a control signal from processor 101 or feedback from oximetry control 102, the system 105 can be switched from ventilator mode to fixed flow rate mode, the latter being more suitable for patients capable of breathing on their own. Other fixed or variable flow rates may be elected via control signals from processor 101 or feedback from oximetry control 102.

With the present invention, a single therapy unit can combine emergency cardiac defibrillation and pulmonary oxygen administration in one convenient casing. An electrocardio diagnosis/monitoring/defibrillation device can be combined with electropulmonary blood oximetry/oxygen administration, including automated patient cardiopulmonary oxygen assessment and voice prompted therapy and resuscitation.

Although described herein as an interactive combination of oxygen delivery, oximetry and defibrillation systems, it will be apparent that the invention could be comprised of a combination of any two of these systems, with associated modification of the control mechanisms and voice prompts, as will be evident to those of skill in the art.

What is claimed is:

[1. A hand-held multi-component emergency medical system, comprising:

a breathable oxygen delivery system;

a defibrillation system; and a unitary casing for housing said oxygen delivery system and said defibrillation system.]

[2. A hand-held multi-component emergency medical system, comprising:

a breathable oxygen delivery system;

a oximetry system;

a defibrillation system; and a unitary casing for housing said oxygen delivery system, said oximetry system and said defibrillation system.]

[3. A system as claimed in claim 1 or 2, further comprising a voice prompting system for directing a user through a protocol employing said defibrillation system.]

[4. A system as claimed in claim 1 or 2, further comprising a voice prompting system for directing a user through a protocol employing said defibrillation system and said oxygen delivery system.]

[5. A system as claimed in claim 2, further comprising a voice prompting system for directing a user through a protocol employing said defibrillation system, said oxygen delivery system and said oximetry system.]

[6. A system as claimed in claim 5, further comprising a control processor for controlling operations of at least said defibrillation system, said voice prompting system and said oximetry system.]

[7. A system as claimed in claim 6, wherein said control processor further controls said oxygen delivery system.]

[8. A system as claimed in claim 7, further comprising a feedback control from said oximetry system to said oxygen delivery system to regulate oxygen delivery.]

[9. A system as claimed in claim 8, further including a display system coupled to said oximetry system.]

[10. A system as claimed in claim 8, further including means for modal control of said oxygen delivery system, for switching or prompting a user to switch said oxygen delivery system between a variable flow rate/pressure cyclic ventilator mode and a fixed flow rate mode.]

*11. A multi-component emergency medical system of a size and weight which can easily be carried by a single hand comprising:*

*a breathable oxygen delivery system;*

*a prompting system for directing a user through a protocol employing said oxygen delivery system; and*

*a unitary casing for housing said oxygen delivery system and said prompting system; the cumulative size and weight of the unitary casing, oxygen delivery system, and prompting system such that the unitary casing, when housing the oxygen delivery system and the prompting system, can easily be carried by a single hand.*

*12. A multi-component emergency medical system of a size and weight which can easily be carried by a single hand comprising:*

*a breathable oxygen delivery system;*

*a capnometer;*

*and a unitary casing for housing said oxygen delivery system and said capnometer; the cumulative size and weight of the unitary casing, oxygen delivery system, and capnometer such that the unitary casing, when housing the oxygen delivery system and the capnometer, can easily be carried by a single hand.*

*13. A system as claimed in claim 12, further comprising a control processor for controlling the operation of said oxygen delivery system on the basis of feedback from the capnometer.*

*14. A system as claimed in claim 12, further comprising a control processor for controlling the operation of said oxygen delivery system on the basis of feedback from the capnometer.*

*15. A system as claimed in claim 12, further including a display system coupled to said capnometer for at least one of assessing, diagnosing and monitoring.*

*16. A system as claimed in claim 12, further comprising a prompting system.*

*17. A system as claimed in claim 16, further comprising a control processor for controlling the prompting system to direct the user through a protocol of operation of the oxygen en delivery system on the basis of feedback from the capnometer.*

*18. A system as claimed in claim 12, further comprising an oximeter.*

*19. A system as claimed in claim 18, further comprising a control processor for controlling the operation of said oxygen delivery system on the basis of feedback from both the oximeter and the capnometer.*

*20. A system as claimed in claim 18, further comprising a control processor for controlling the operation of said oxygen delivery system on the basis of feedback from both the oximeter and the capnometer.*

*21. A system as claimed in claim 18, further including a display system coupled to said oximeter and capnometer for at least one of assessing, diagnosing and monitoring.*

*22. A system as claimed in claim 18, further comprising a prompting system.*

*23. A system as claimed in claim 22, further comprising a control processor for controlling the prompting system to direct the user through a protocol of operation of the oxygen delivery system based on feedback from both the oximeter and the capnometer.*

*24. A multi-component emergency medical system of a size and weight which can easily be carried by a single hand comprising:*

*a breathable oxygen delivery system;*

*an oximeter;*

*a prompting system;*

*and a unitary casing for housing said oxygen delivery system and said oximeter and said prompting system; the cumulative size and weight of the unitary casing, oxygen delivery system, oximeter, and prompting system such that the unitary casing, when housing the oxygen delivery system, the oximeter, and the prompting system, can easily be carried by a single hand.*

*25. A system as claimed in claim 24, further comprising a control processor for controlling the prompting system to direct a user through a protocol of operation of the oxygen delivery system based on feedback from the oximeter.*

*26. A multi-component emergency medical system of a size and weight which can easily be carried by a single hand comprising:*

*a breathable oxygen delivery system;*

*an oximeter;*

*a display system coupled to said oximeter for at least one of assessing, diagnosing and monitoring;*

*and a unitary casing for housing said oxygen delivery system and said oximeter and said display system; the cumulative size and weight of the unitary casing, oxygen delivery system, oximeter, and display system such that the unitary casing, when housing the oxygen delivery system, the oximeter, and the display system, can easily be carried by a single hand.*

*27. A system as claimed in claim 26, further comprising a prompting system.*

*28. A system as claimed in claim 24 or 26, further comprising a control processor for controlling the operation of said oxygen delivery system on the basis of feedback from the oximeter.*

*29. A system as claimed in claims 11, 12, 24, or 26, of a size and weight which can be hand-held.*

*30. A system as claimed in claims 11, 12, 24, or 26, of a size and weight which can be wearable.*

*31. A system as claimed in claim 25, 17, or 23 further including means for modal control of said oxygen delivery system, for switching or prompting a user to switch said oxygen delivery system between a variable flow rate/pressure cyclic ventilator mode and a fixed flow rate mode.*

* * * * *